(12) United States Patent
Fugerer et al.

(10) Patent No.: US 12,239,498 B2
(45) Date of Patent: Mar. 4, 2025

(54) APPARATUS AND METHOD FOR TOOL ACCESSORY IDENTIFICATION

(71) Applicant: Arthrex, Inc., Naples, FL (US)

(72) Inventors: Robert Fugerer, Lutz, FL (US); John Batikian, Pismo Beach, CA (US); Edwin Floyd, Naples, FL (US)

(73) Assignee: Arthrex, Inc., Naples, FL (US)

( * ) Notice: Subject to any disclaimer, the term of this patent is extended or adjusted under 35 U.S.C. 154(b) by 171 days.

(21) Appl. No.: 17/543,795

(22) Filed: Dec. 7, 2021

(65) Prior Publication Data

US 2023/0172687 A1  Jun. 8, 2023

(51) Int. Cl.
G08B 21/00 (2006.01)
A61B 17/00 (2006.01)
A61B 90/98 (2016.01)

(52) U.S. Cl.
CPC ............. *A61B 90/98* (2016.02); *A61B 17/00* (2013.01); *A61B 2017/00199* (2013.01); *A61B 2017/00482* (2013.01)

(58) Field of Classification Search
CPC .................... A61B 90/98; A61B 17/00; A61B 2017/00199; A61B 2017/00482; G16H 40/63
See application file for complete search history.

(56) References Cited

U.S. PATENT DOCUMENTS

| | | | |
|---|---|---|---|
| 7,422,582 B2 | 9/2008 | Malackowski et al. | |
| 7,983,865 B2 | 7/2011 | Shimizu | |
| 7,998,157 B2 | 8/2011 | Culp et al. | |
| 8,035,487 B2 | 10/2011 | Malackowski | |
| 8,986,302 B2 | 3/2015 | Aldridge et al. | |
| 9,072,895 B2 | 7/2015 | Mate et al. | |
| 9,707,026 B2 | 7/2017 | Malackowski et al. | |
| 9,888,955 B2 | 2/2018 | Hosier | |
| 10,265,117 B2 | 4/2019 | Wiener et al. | |
| 10,338,259 B2 | 7/2019 | Calderoni et al. | |
| 10,760,932 B2 | 9/2020 | Zemlok | |
| 11,002,872 B2 | 5/2021 | Calderoni et al. | |
| 2002/0032435 A1 | 3/2002 | Levin | |
| 2003/0088295 A1* | 5/2003 | Cox | G16H 20/30 607/60 |
| 2009/0259149 A1 | 10/2009 | Tahara et al. | |
| 2011/0093284 A1* | 4/2011 | Dicks | G16H 40/67 705/2 |
| 2014/0357309 A1* | 12/2014 | Leabman | H02J 50/10 455/522 |

(Continued)

FOREIGN PATENT DOCUMENTS

CN 203232105 U 10/2013
EP 1308184 A2 5/2003

*Primary Examiner* — Mark S Rushing
(74) *Attorney, Agent, or Firm* — Price Heneveld LLP

(57) ABSTRACT

A surgical device controlled by a control console includes a device body, an identification circuit in connection with the device body, and a communication interface. The communication interface is configured to communicatively connect the identification circuit to the control console. In response to receiving an energization signal from the control console via the communication interface, the identification circuit activates an identification signal at a fixed frequency for a predetermined period of time and communicates the identification signal to the control console via the communication interface.

19 Claims, 6 Drawing Sheets

(56) References Cited

U.S. PATENT DOCUMENTS

2015/0150546 A1* 6/2015 Goldschmidt ......... A61B 90/90
                                                  606/1
2015/0272608 A1* 10/2015 Gladstone .......... A61B 17/1626
                                                 606/167
2017/0172667 A1* 6/2017 Charles ................... A61F 9/007

* cited by examiner

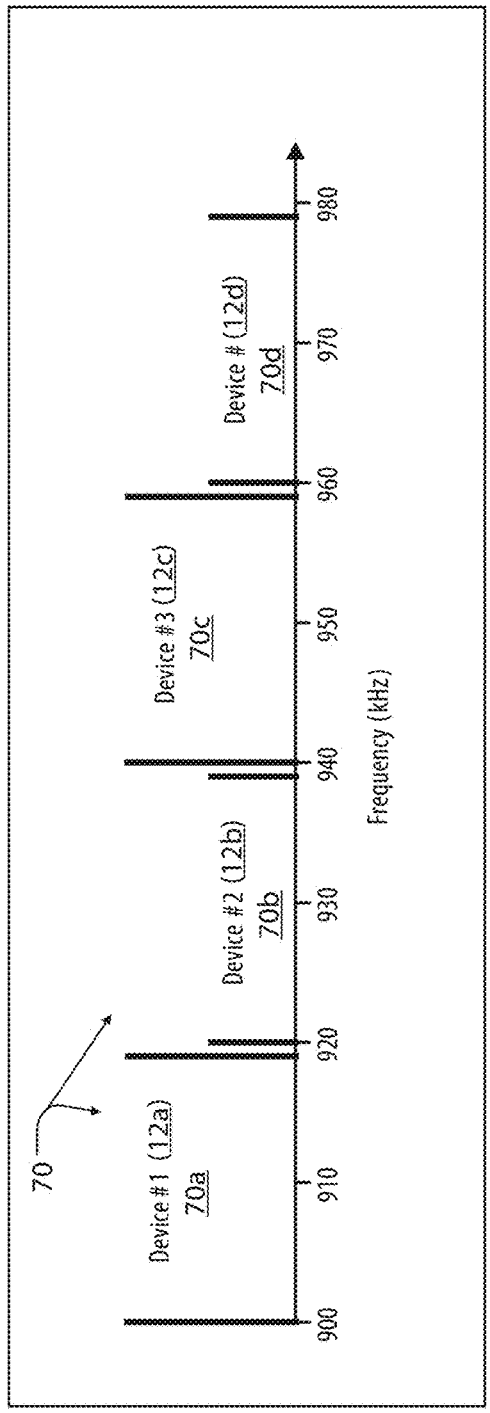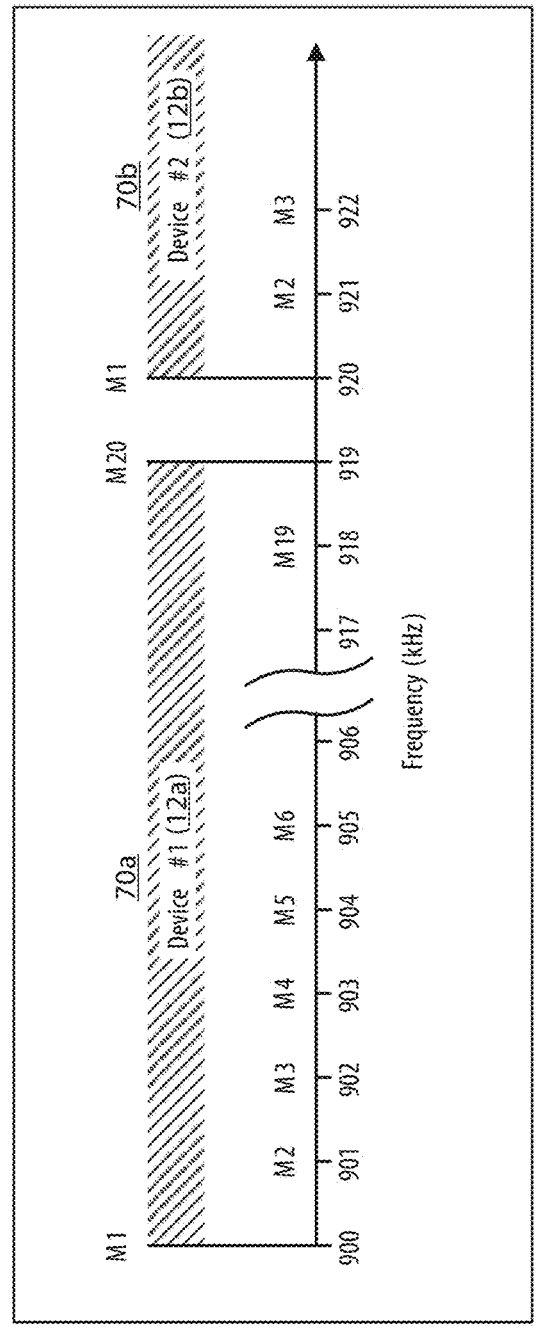
FIG. 4A
FIG. 4B

APPARATUS AND METHOD FOR TOOL ACCESSORY IDENTIFICATION

BACKGROUND

The present disclosure generally relates to a system and method for detecting a surgical device in connection with a control console. The identification of the surgical device may allow a control system of the control console to tailor or customize the operation of the control console to suit the specific operating parameters for each of the surgical devices that may be interchangeably connected for operation. The improved operating methods and techniques may provide for the control system of the control console to accurately identify the surgical device even when operated in environments that are not conducive to maintaining signal fidelity.

SUMMARY

The disclosure provides for systems and methods for identifying device configurations of a wide variety of devices implemented in medical and surgical environments. In various implementations, the system comprises a control console or controller configured to interchangeably control a plurality of surgical devices. The surgical devices may correspond to devices or accessories, each of which may have a different device configuration (e.g., inputs, outputs, actuators, features, etc.) suited to a particular use and application. To support the control of such a wide range of devices, the disclosure provides for a method that identifies one or more repeating, periodic properties of an identification signal to identify a connected device. Once identified, the controller may assign a control configuration to interface with the connected device via a predefined or stored input/output configuration. In this way, the system may provide for robust identification and operation of a variety of devices.

In some implementations, the disclosure provides for a system comprising a control console configured to interchangeably control a plurality of surgical devices. The system comprises at least one communication port in connection with the control console that receives a communication cable configured to communicatively connect to the plurality of surgical devices. A controller is in communication with the at least one communication port and configured to supply an activation signal via the at least one communication port to at least one connected device of the plurality of surgical devices. The controller is further configured to receive at least one identification signal from an identification device of the connected device in response to the activation signal and identify a frequency of the identification signal communicated over a predetermined time. In response to the frequency of the identification signal, the controller identifies at least one device configuration of the connected device.

In various implementations, the disclosure further provides for one or more of the following features alone or in combination:
- the controller is further configured to apply a control configuration of the control console in response to the device configuration and supply control signals to the connected device according to the control configuration;
- the control configuration comprises at least one of the following configurations of the connected device: an operating range of an actuator of the connected device, an input configuration, and a control signal protocol;
- the controller is further configured to identify a plurality of different frequencies of the at least one identification signal and apply a distinct control configuration for each of the plurality of surgical devices in response to each of the different frequencies;
- each of the plurality of different frequencies is interpreted by the controller to distinguish the control configurations of the plurality of surgical devices;
- the controller is further configured to identify each of the surgical devices within one of a plurality of frequency ranges in response to the frequency of the identification signal;
- the frequency ranges are non-overlapping frequency bands and the controller distinctly identifies one of the plurality of surgical devices in response to the frequency of the identification signal within each of the non-overlapping frequency bands;
- the controller is further configured to identify a plurality of messages for each of the surgical devices in response to a plurality of different periods of the frequency of the identification signal within one of the frequency ranges;
- each of the messages indicates a different control instruction or status indication of the connected device;
- each of the surgical devices comprises an identification device, where the identification device generates the identification signal in response to the activation signal;
- the control console further comprises a user interface, wherein the controller controls the user interface to display operating data in response to the device configuration of the connected device;
- the at least one communication port comprises a plurality of communication ports comprising a plurality of channels, wherein the controller is further configured to identify a first device configuration of a first device of the plurality of surgical devices in response to a first frequency of a first identification signal and identify a second device configuration of a second device of the plurality of surgical devices in response to a second frequency of a second identification signal;
- the controller is further configured to supply first control signals to the first device via a first channel of the plurality of channels based on a first control configuration identified in response to the first device configuration and supply second control signals to the second device via a second channel of the plurality of channels based on a second control configuration identified in response to the second device configuration;
- the first control configuration and the second control configuration are concurrently applied by the controller;
- the at least one surgical device comprises at least one of a peripheral device, a surgical tool, and a surgical detection or measurement device; and/or
- the identification device comprises an oscillator configured to communicate the identification signal at a fixed frequency.

In some implementations, the disclosure provides a method for controlling a plurality of surgical devices via a control console. The method includes supplying an activation signal to a connected device via a communication port and receiving an identification signal from an identification device of the connected device for a predetermined period of time. The method further comprises identifying a frequency of the identification signal. In response to the frequency, the method continues by identifying a device configuration of the connected device. The device configuration corresponds to a first device of the plurality of surgical devices. The method further comprises controlling an operation of the first device in response to the device configuration. The device configuration identifies an interface configuration of at least one input of the first device.

In various implementations, the disclosure further provides for one or more of the following features alone or in combination:

the control console receives the identification signal at a different frequency from each of the surgical devices and distinguishes among the surgical devices in response to the different frequencies;

the identification device of each of the plurality of surgical devices communicates the identification signal at a different frequency;

each of the surgical devices is identified in response to the frequency of the identification signal within a frequency range; and the method further comprises identifying a status of the connected device in response to the frequency of the identification signal within a first range of the frequency ranges, the first range corresponding to the first device;

the frequency of the identification signal identifies a device configuration of the at least one surgical device; and/or the frequency of the identification signal is a fixed frequency identified by the control console by identifying a timing or a rising or falling edge of the identification signal.

In some implementations, the disclosure provides for a surgical device controlled by a control console. The device comprises a device body, an identification circuit in connection with the device body, and a communication interface. The communication interface is configured to communicatively connect the identification circuit to the control console. In response to receiving an energization signal from the control console via the communication interface, the identification circuit activates an identification signal at a fixed frequency for a predetermined period of time and communicates the identification signal to the control console via the communication interface. In some implementations, the device may further comprise an accessory actuator configured to control a movement of a connected accessory and a device controller disposed in the device body. The device controller may be configured to control the operation of the accessory actuator in response to control signals received from control console. The device controller may further be in communication with the identification circuit and assign the frequency of the identification signal in response to a device configuration of the surgical device and a message associated with the operation of the surgical device.

These and other features, objects and advantages will become apparent upon reading the following description thereof together with reference to the accompanying drawings.

BRIEF DESCRIPTION OF THE DRAWINGS

FIG. 4A is a frequency plot demonstrating a plurality of frequency bands of identification signals corresponding to each of a plurality of surgical devices;

FIG. 4B is a detailed plot of a frequency band of a surgical device demonstrating a plurality of messages or status indicators identified by a control console from an identification signal;

DETAILED DESCRIPTION

Figure 1:
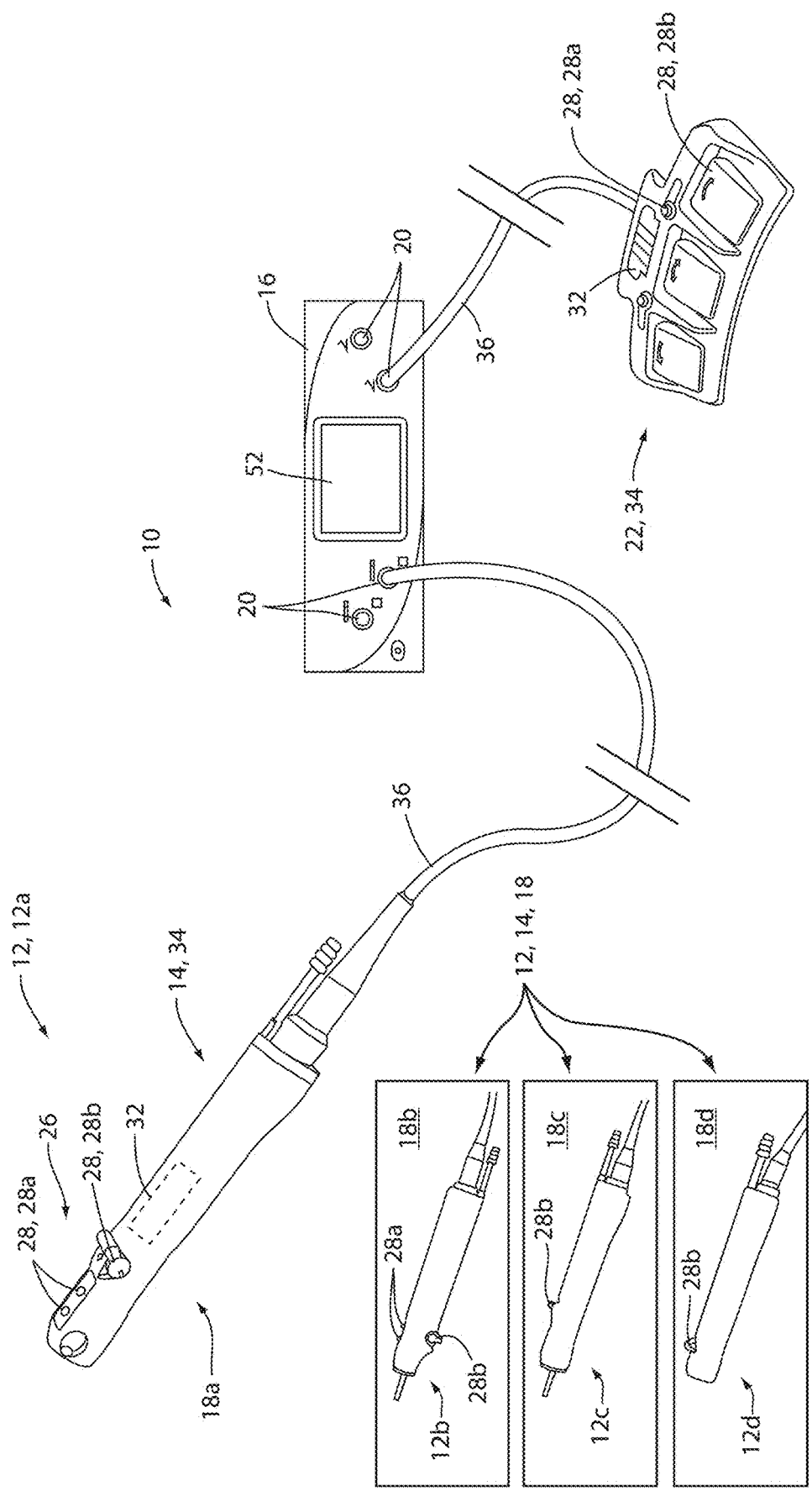
FIG. 1 is a diagram demonstrating a control system comprising a control console configured to interchangeably interface with a plurality of surgical devices exemplified as surgical handpieces.

The disclosure generally provides for a system comprising a control console or control unit configured to interchangeably connect to and control a plurality of surgical devices. The surgical devices may correspond to various devices or accessories that may be implemented in medical or surgical environments. As described in some of the following examples, the surgical devices interfaced with the control console correspond to surgical handpieces, each of which may include one or more configuration or operational variations. Accordingly, the control console of the disclosed system may be required to identify the configuration of the surgical device connected to the control console in order to interpret input signals and output compatible control signals. For example, based on the device configuration, the control console may be configured to communicate via one or more communication protocols, input/output configurations and various control configurations. In this way, the system may provide for a rapid interfacing and configuration process to adjust the operation of the control console in accordance with preconfigured or custom control schemes for each of the device configurations of the various compatible surgical devices.

In order to identify the device configuration (e.g., a type, model, style, etc.) of the surgical device and the corresponding control configuration, the control console may initially communicate with a connected surgical device to receive a periodic identification signal that may be communicated at a fixed or constant target frequency for a predetermined period of time. Based on the temporal frequency of the identification signal, the controller of the control console may identify a type, model, and/or style and, thus, the configuration of the connected surgical device. By communicating the signal at a continuous target frequency for a predetermined time period, the control console may identify the frequency and the corresponding device configuration even in noisy or harsh environments that may cause fidelity issues in the identification signal. For example, if the identification signal were to be distinguished based on different an analog voltage values (e.g., 1V, 2V, 3V, etc.), variations in the voltage values in noisy environments could result in misidentification and operating errors. Accordingly, the disclosure provides for systems and methods to accurately communicate the identification signal to the control console by avoiding issues that may result from the operating environment as well as the connection integrity of a wired connection interface of the system. The following exemplary systems and methods may be implemented with a wide variety of surgical devices or accessories to communicate identifications signals identifying a model, status, and/or various control messages. The identification signals may be interpreted or identified even when exposed to noisy ambient conditions, thereby providing for robust operation of the control system.

Figure 2:
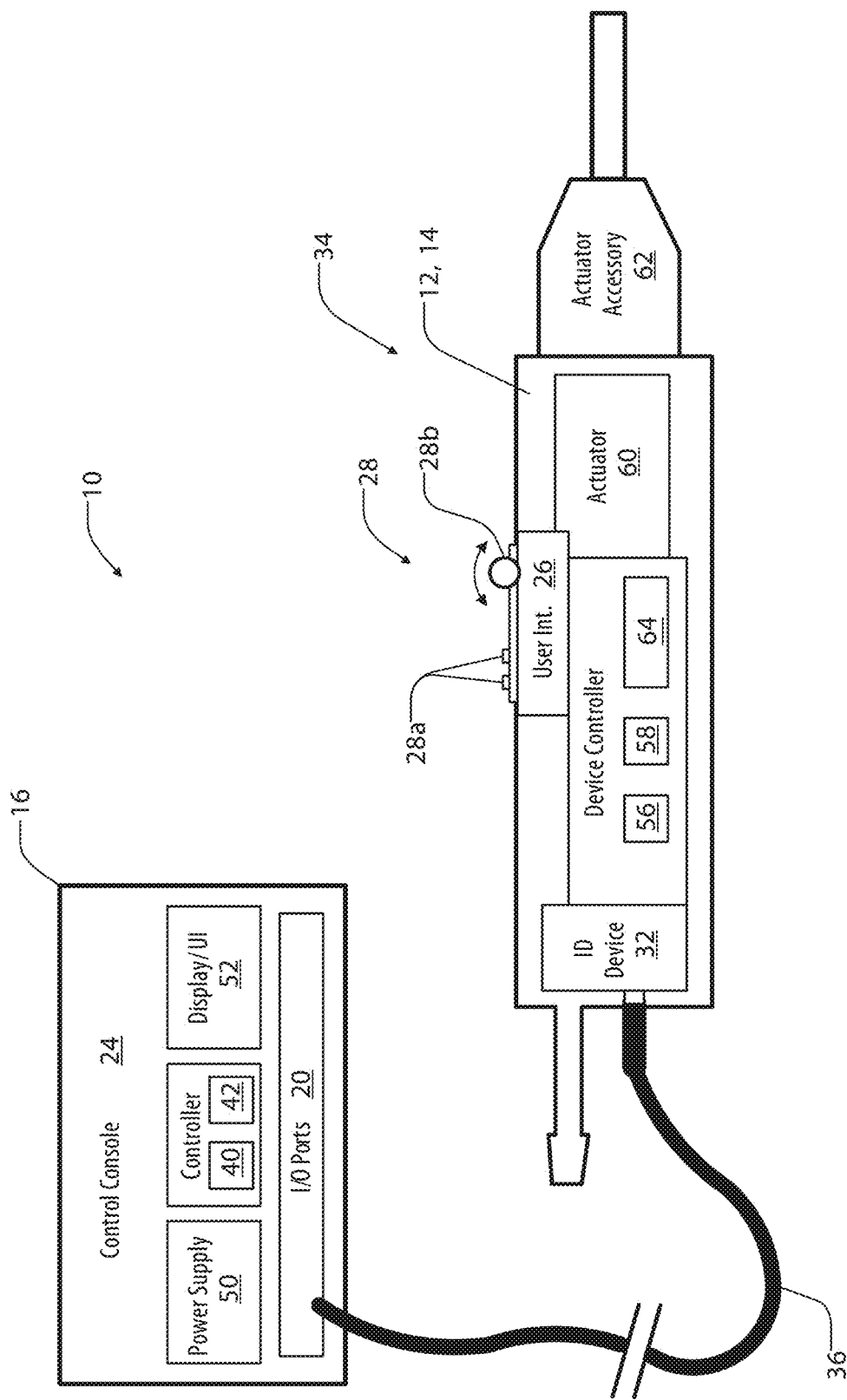
FIG. 2 is a schematic diagram of a control console interfaced with an exemplary surgical device.

Referring now to FIGS. 1 and 2, an exemplary diagram of a control system 10 for a surgical device 12 is shown. The surgical device 12 may correspond to a surgical tool, input control device, or related accessory and is exemplified in the form of a handheld instrument or handpiece 14 that is powered via a control console 16. Though the surgical device 12 may correspond to various devices and peripherals compatible with the control console 16, each of the exemplary surgical devices may be referred to in reference to specific examples for clarity. Accordingly, though handpieces 14 are discussed in various examples, it shall be understood that the disclosure is broadly applicable to various medical devices, accessories, peripherals, and related devices that may be controlled by the control console 16. In operation, the control console 16 may supply operating power and control signals to the handpieces 14, each of which may have a different device or operating configuration 18. In addition to the various configurations 18 of the surgical devices 12, the control console 16 may comprise multiple control or communication ports 20 configured to concurrently interface with multiple surgical devices 12 or peripheral devices 22 over a plurality of channels.

The variety of device configurations 18 may be the result of the various configurations of user interfaces 26, actuators, or features of the surgical devices 12. For example, each of the surgical devices 12 may require different control signals from a controller 24 of the control console 16 to effectuate a desired operation. Accordingly, the controller 24 may be required to configure the operation of the communication ports 20 and corresponding input/output (I/O) circuits to recognize and interpret different input signals from input devices 28 and communicate corresponding control outputs. For example, each of the handpieces 14 may include pushbutton interfaces 28a (e.g., momentary switches, alternate action, etc.), variable switches 28b, or various input devices and combinations to suit the operating requirements. Additionally, the handpieces 14 may have different supply or control requirements (voltages, control signals, communication protocols, etc.) as a result of differences in hardware (e.g., motor or actuator types, drive power, etc.). Accordingly, the system 10 may rely on adaptive programming to facilitate the operation of the diverse configurations 18 of the handpieces 14.

In operation, the controller 24 may receive an identification signal 30 from an identification module or device 32 of a connected device 34 of the surgical devices 12. The connected device 34 may be connected via a connection interface 36 (e.g., a power and/or communication cable or wired connection) to one of the communication ports 20 and interfaced via one of a plurality of control channels. As discussed in greater detail in the following examples, the identification signal 30 is interpreted or processed by the controller 24 to determine an identifier (e.g., a tool ID) indicating a make, model, style, specification, and/or operating configuration of the connected device 34. In response to the determination of a model or type (e.g., an identifier) of the connected device 34, a processor 40 of the controller 24 may access a table or identification key in a memory 42 to determine and assign the corresponding control configuration 18 for the connected device 34. Once the controller 24 of the console 16 is configured in accordance with the operating configuration 18 of the connected device 34, the controller 24 may accurately supply operating power and/or control signals to the connected device 34 in response to inputs to the user interface 26.

As discussed herein, the surgical devices 12, handpieces 14, and peripheral devices 22 may provide for a diverse range of specialized applications supported by the various device configurations 18. For example, the surgical devices 12 or handpieces 14 may provide for a variety of medical or surgical operations including, but not limited to, sectioning, burring, grinding, cutting, and drilling, as well as incision operations, suction control, or other powered surgical operations. In the exemplary embodiment shown, the handpieces 14 corresponds to a motorized shaver system that may be used for the resection of soft tissue, cartilage, and bone during arthroscopic surgical procedures. Though discussed in reference to specific examples, the control system 10 may similarly be applied to control various surgical implements and provide corresponding operating configurations.

In addition to the configuration of the user interface 26 incorporated on the handpiece 14, additional peripheral devices 22 or accessories (e.g., footswitches, pedals, remote controls, etc.) may similarly be connected to the communication ports 20 of the control console 16 and may also include the identification device 32. In this configuration, the controller 24 of the control console 16 may be configured to operate in response to various control inputs associated with the input devices 28 of the peripheral devices 22. Accordingly, the controller 24 may receive the identification signal 30 from the identification module or device 32 incorporated in one or more connected peripheral devices 22 and configure the operation of the control console 16 to communicate with the peripheral devices 22. In this way, the system 10 may provide for the peripheral devices 22 to be implemented as control devices for the surgical devices 12 or handpieces 14 by supplying input signals to the controller 24 via one or more of the input devices 28. As previously discussed, the handpieces 14 and peripheral devices 22 may generally be referred to as the surgical devices 12, and the corresponding device configurations 18 may be identified by the controller 24 of the control console 16 for operation.

Figure 3:
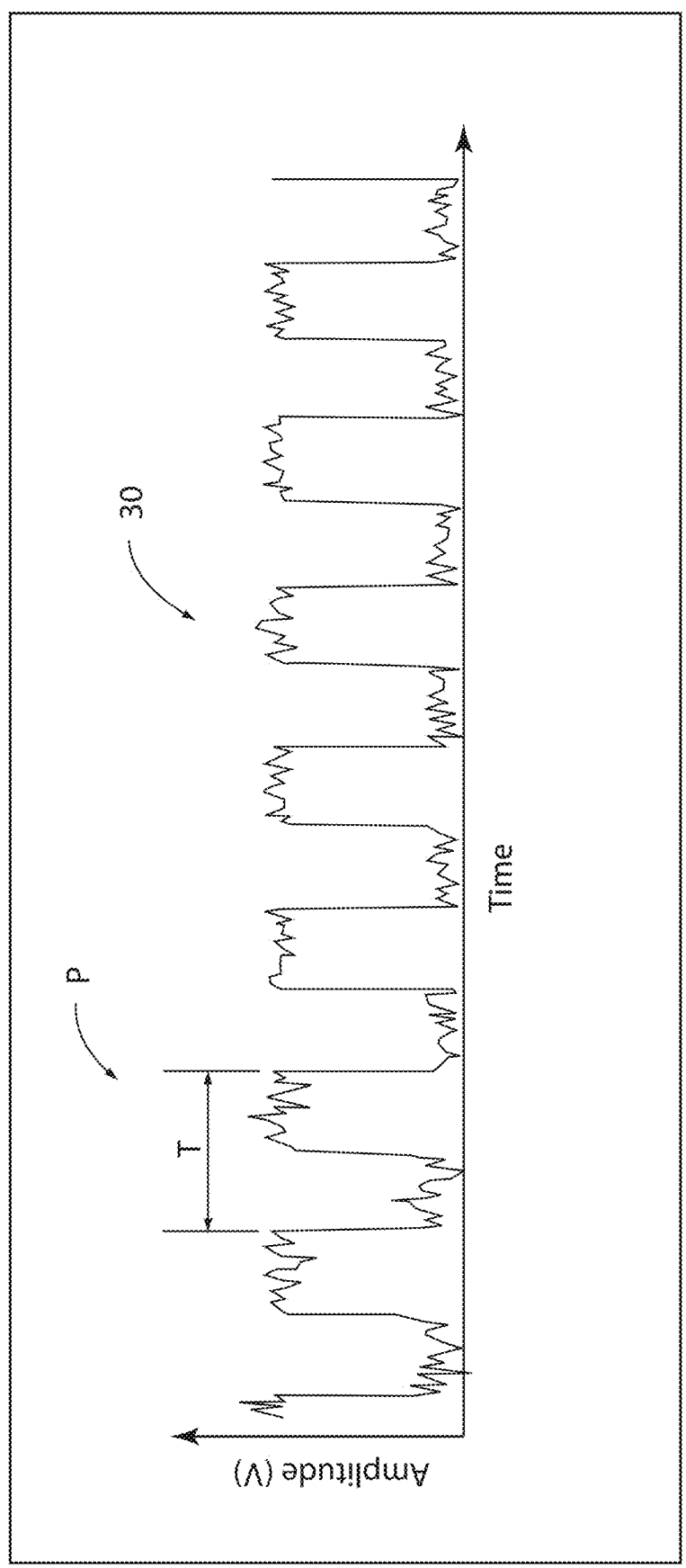
FIG. 3 is a plot demonstrating an exemplary identification signal communicated from a communication device of a surgical handpiece.

Referring now to FIGS. 1-3, detailed examples of the identification signals and methods for identifying the operating configuration of the connected device 34 are provided. As previously discussed, the communication of the identification signal 30 may be susceptible to interference, particularly in the form of electromagnetic interference (EMI), which may be common in the operating environment (e.g., a surgical suite, hospital, etc.) of the system 10. The interference may be the result of the operation of multiple electronic devices in an operating room. In order to limit the vulnerability of the interpretation of the identification signal 30 by the controller 24 to interference, the system 10 may communicate the identification signal 30 as a periodic signal with a fixed target frequency as exemplified in FIG. 3. For example, the identification signal 30 may correspond to a periodic signal with a temporal frequency defined as the inverse of the period T. The time of the period T and the corresponding frequency of the identification signal 30 may vary broadly depending on the application of the system 10 and each frequency or frequency band of the identification signal 30. Based on the frequency identified by the controller 24 or processor 40, the corresponding device configuration 18 of the connected device 34 may be attributed by the controller 24 to a style, model, or device configuration 18 of the surgical devices 12. The identification signal 30 may be communicated for a predetermined period of time that may extend for a duration of at least two or more times the period T (e.g., 3T, 4T, or longer durations).

In general, the identification device 32 may generate the identification signal 30 at a frequency compatible with an identification range of an identification circuit (e.g., processor 40 or an integrated circuit) of the controller 24. The identification signal 30 may be easily distinguished, even when exposed to significant noise as depicted in FIG. 3, from other signals or messages due to the fixed target period extending over a predetermined time. In this configuration, the controller 24 may detect the frequency of the identification signal 30 over a detection duration of multiple periods T of the frequency or as an average frequency to exclude outlying frequencies and noise to ensure that frequency is accurately identified. In some examples, the frequency of the identification signal 30 may even be dithered or adjusted over time by the identification device around a target frequency. In this way, the controller 24 may identify the average frequency of the identification signal 30 as the target frequency associated with the device configuration 18 of the connected device 34 and filter or prevent harmonic noise to further support the identification of the device configuration 18 in particularly noisy environments. Accordingly, the repetitive, oscillating nature of the identification signal 30 may allow the controller 24 to determine the identifier (e.g., a tool ID) of the handpiece 14 or surgical device 12 without failures dues to nearby signal interference. The operating range of the frequency for the identification signal 30 may vary from approximately 100 Hz to 10 MHz in different applications. For practical purposes, the identification signal may include frequencies ranging from 500 Hz to 1 MHz. However, the frequency of the identification signal 30 may be implemented outside the exemplary ranges described.

The identification signal 30 in the exemplary case depicted is a square wave generated by the identification device 32. As demonstrated, the square wave includes noise induced oscillations and variations in voltage. However, the pattern and timing (e.g., period T) of the identification signal 30 is not affected by the interference and may readily be interpreted by the controller 24. Though demonstrated as a square wave, the identification signal 30 may be implemented as various periodic signals, such as sine waves, triangle waves, saw tooth waves, etc. The identification device 32 may be implemented with suitable capability to generate the identification signal 30 at a frequency and pattern that is compatible for interpretation by the processor 40 or processing circuitry of the controller 24. In an exemplary implementation, the identification device 32 may operate with limited power requirements with a voltage of 5V or less. The identification device 32 may be implemented as an oscillator, particularly in cases where the identification signal 30 is fixed throughout the life of the handpiece, and may implement more sophisticated processing or signal generation devices in more complex applications as discussed in later examples. In such cases, the identification module or device 32 may be implemented as a microprocessor, microcontroller, or application-specific integrated controller (ASIC), which may be implemented as a distinct device or in combination with the operating circuitry (e.g., device controller 54) of the handpiece 14.

Referring now to FIG. 2 in further detail, the control console 16 is shown connected to the handpiece 14 via the connection interface 36. In addition to the aspects of the control console 16 that were previously introduced, the control console 16 may further comprise a power supply 50 and display or user interface 52. The specifications of the power supply 50 may provide for operating power of each of the surgical devices 12 (e.g., handpieces 14, peripheral devices 22, etc.) via the communication ports 20, as well as operating power for the controller 24 and display/user interface 52 of the control console 16. The display/user interface 52 may correspond to various display devices (e.g., a liquid crystal display), which may incorporate touch panel functionality in addition to various switches or conventional input devices.

The varying nature of the compatible handpieces 14 or surgical devices 12 and their broad range of corresponding efficacies may result in a wide variety of operating configurations and corresponding circuitry incorporated in the connected device 34. In the example provided in FIG. 2, the surgical device 12 or handpiece 14 may include a device controller 54 that may incorporate a processor 56 and memory 58 that may be configured to communicate and interpret operating signals to the controller 24 of the control console 16 via the connection interface 36 and the communication ports 20. In this configuration, inputs received by the input devices 28 of the user interface 26 of the handpiece 14 may be communicated to the device controller 54 and transmitted to the console controller 24 to adjust and control the operation of the handpiece 14. The device controller 54 may further be in communication with an actuator 60, which may correspond to an electrical motor and drive mechanism that may generate rotational motion and/or translational motion for a connected actuator accessory 62. In various implementations, the actuation accessories 62 may correspond to reciprocating or rotating cutting or oscillating blades that may be implemented in surgery for surface preparations, resections, and/or various cutting or burring operations. For example, the actuator accessories 62 may be configured to drive various saws, drills, burrs, wraps, or similar cutting tools.

Though discussed primarily in reference to the actuator 60 as a motorized device, the surgical device 12 may ultimately correspond to a variety of medical devices (e.g., lasers/radio frequency ablation devices, pumps, vacuums/suction devices, imagers, etc.), which similarly may be interfaced with the control console 16 based on the corresponding device configuration 18 communicated from the identification device 32. As previously discussed, the identification device 32 may be implemented into the surgical device 12 as a discrete device or incorporated in the device controller 54 as an integrated component or module. Accordingly, the identification device 32 may be implemented in a wide variety of applications to identify the device configuration 18 or operating configuration of the surgical device 12 for control or communication via the control console 16.

In some embodiments, the surgical device 12 may further comprise a communication circuit 64 that may be configured to communicate via a plurality of wired or wireless communication protocols. In an exemplary implementation, the communication circuit 64 may correspond to a wireless communication interface that may provide for communication to or from the actuator accessory 62. For example, the communication circuit 64 may provide for communication to and/or from the actuator accessory 62 via the device controller 54 (e.g., processor 56, memory 58). In this way, the device controller 54 may identify an accessory type, configuration, etc. of the actuator accessory 62. In some examples, the accessory type of the actuator accessory 62 may be communicated from the device controller 54 to the console controller 24 as a message M incorporated in the identification signal 30. As further discussed, the message M may be interpreted by the controller 24 in response to the frequency of the identification signal 30. In this way, the controller 24 may configure the operation of the control console 16 based on the device configuration 18 as well as the accessory type of the actuator accessory 62. The communication circuit 64 may be configured to communicate in accordance with a variety of communication protocols and include corresponding operating circuitry. For example, the communication circuit 64 may provide for a wired communication interface (e.g., serial, Universal Serial Bus (USB), Universal Asynchronous Receiver/Transmitter (UART), etc.) and/or a wireless communication interface (e.g., a ZigBee, an Ultra-Wide Band (UWB), Radio Frequency Identification (RFID), infrared, Bluetooth®, Bluetooth® Low Energy (BLE), Near Field Communication (NFC), etc.

Referring now to FIGS. 4A and 4B, the console controller 24 of the control system 10 may be configured, in some cases, to identify multiple bits or messages of information based on the frequency of the identification signal 30. As shown in FIG. 4A, a plurality of frequency bands 70 may be designated to identify and distinguish among the surgical devices 12. As show, a first frequency band 70*a* may be assigned to a first device 12*a* and range from 900 kHz to 919 kHz. Additional surgical devices 12 may include a second device 12*b* identified by a second frequency band 70*b* ranging from 920 kHz to 939 kHz, a third surgical device 12*c* identified by a third frequency band 70*c* ranging from 940 kHz to 959 kHz, and a fourth device 12*d* identified over a fourth frequency band 70*d* ranging from 960 kHz to 979 kHz. Accordingly, based on the frequency bands 70 demonstrated in FIG. 4A, the controller 24 may interpret the frequency of the identification signal 30 within each of the frequency bands 70 to identify the device configuration 18 of the corresponding surgical device 12. For example, in response to receiving the identification signal 30 and identifying that the frequency is within the first frequency band 70*a*, the controller 24 may identify that the first device 12*a* is the connected device 34. Similarly, in response to identifying that the frequency of the identification signal 30 is within the second frequency band 70*b*, the controller 24 may identify the connected device 34 as the second device 12*b*. Accordingly, the controller 24 of the control console 16 may identify the connected device 34 based on the identification signal 30 communicating a frequency within one of the frequency bands 70.

Referring now to FIG. 4B, detailed plots of the first frequency band 70*a* and the second frequency band 70*b* are depicted. In addition to identifying the type or the identification of the connected device 34 as one of the devices 12*a*, 12*b*, etc.; the controller 24 of the control console 16 may further identify a message M1, M2, M3, etc. or status signal of the connected device 34 in response to a frequency identified within one of the frequency bands 70*a*, 70*b*, etc. For example, as previously introduced, each of the frequency bands 70 includes a range of frequencies. In the example provided, each of the frequency bands 70 extends over a range of 20 kHz. In this configuration, frequencies centered around specific periods or frequency values within each of the frequency bands 70 may be interpreted by the controller 24 to detect specific messages M1, M2, M3, etc. or status indicators. The messages M1, M2, M3, etc. may be further interpreted based on a table or designation in the memory 42 to identify a state, operating condition, and/or operating mode of the connected device 34. As provided in the specific exemplary case depicted, the controller 24 may interpret a first message M1 from the surgical device 12 in response to identifying the frequency of the identification signal 30 centered at 900 kHz. Additional messages M2, M3, and M4 may be identified by the controller 24 in response to the identification signal 30 being centered around corresponding frequencies of 901 kHz, 902 kHz, and 903 kHz, respectively. Accordingly, the communication of the identification signal 30 at a single fixed frequency may be interpreted by the controller 24 of the control console 16 to both identify and discriminate among different surgical devices 12 to identify their corresponding device configurations 18, as well as identify various status messages M1, M2, M3, etc. associated with the operation with the surgical devices 12.

As previously discussed, the sophistication of the identification device 32 may vary based on the operating requirements of the corresponding surgical device 12. In cases where the identification signal 30 is changed to communicate various messages M1, M2, M3, etc. or status indicators, the identification device 32 may be configured to communicate with the device controller 54 to identify a corresponding status or operating message related to the state of the connected device 34. For example, in response to receiving an activation signal or activation energy via the connection interface 36, the device controller 54 may complete a diagnostic check of the connected device 34. Based on the diagnostic check, the device controller 54 may generate one or more messages or identify an operating state (e.g., alive without error, alive with error, motor malfunction, feature failure, etc.) and communicate the corresponding status of the connected device 34 to the identification device 32. In response to the status of the connected device 34 communicated from the device controller 54, the processor 56, or the identification device 32 may access a lookup table and identify the corresponding frequency associated with the status message M1, M2, M3, etc.

Based on the frequency identified in the lookup table or, more generally, the memory 58, the identification device 32 may be instructed to, or otherwise be triggered to, generate the identification signal 30 at the corresponding frequency according to the status message M1, M2, M3, etc. The identification signal 30 may be communicated via the connection interface 36 and interpreted by the controller 24 of the control console 16 to identify both the connected device 34 from the various surgical devices 12*a*, 12*b*, 12*c*, etc. as well as identify the underlying message M1, M2, M3, etc. or status indication associated with the specific frequency of the identification signal 30. Accordingly, the identification signal 30 may be communicated at a fixed frequency for a predetermined period of time and be interpreted by the control console 16 to identify and discriminate among the various connected devices 34 as well as identify an underlying message M1, M2, M3, etc. or status indication of the connected device 34.

Figure 5:
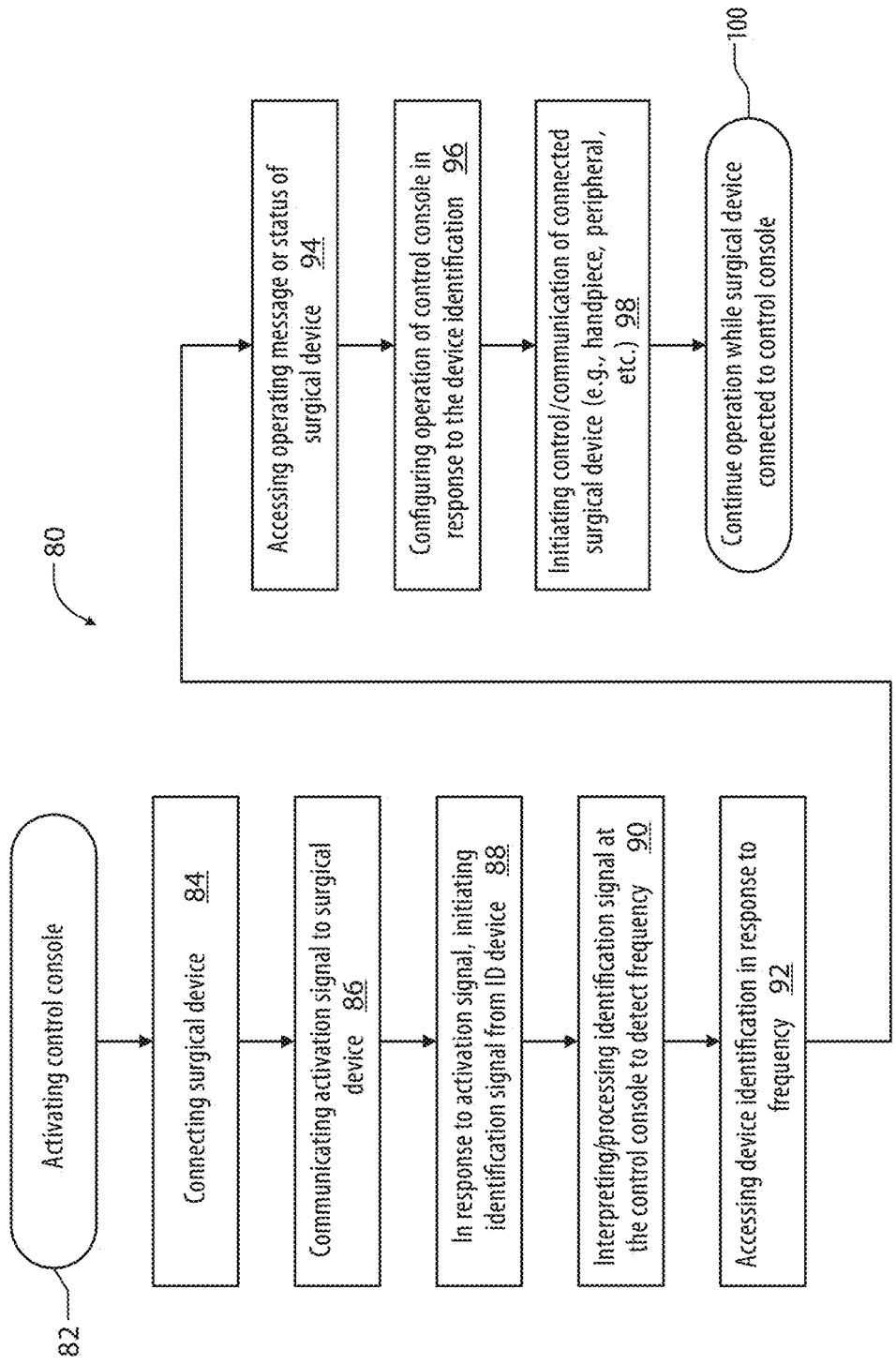
FIG. 5 is an exemplary method for identifying a device configuration of a surgical device interfaced with a control console.

Referring now to FIG. 5, a flowchart is shown demonstrating a method 80 for identifying a surgical device 12 in connection with the control console 16. In operation, the method 80 may begin in response to the activation of the control console at step 82. In addition to the activation of the control console, the surgical device 12 may be connected to one of the communication ports 20 via the connection interface 36 (step 84). In response to the detection of the connected device 34, the controller 24 of the control console 16 may communicate an activation signal to the surgical device 12 (step 86). The activation signal may correspond to a voltage signal or operating power supplied from the communication port 20 of the control console 16 to the device controller 54 of the surgical device 12. Accordingly, the receipt of the activation signal may serve to activate the identification device 32 or the device controller 54 of the surgical device 12, such that the identification signal 30 may be communicated to the control console 16 (step 88).

Once the identification signal 30 is communicated to the controller 24 of the control console 16, the processor 40 or identification circuitry of the controller 24 may interpret the identification signal 30 to detect the frequency (step 90). In response to identifying the frequency of the identification signal 30, the controller 24 may access the device identification 18 of the connected device 34 (step 92). As previously discussed, the device identification (e.g., ID) may indicate the device configuration 18 of the connected device 34, which may be accessed via the memory 42 via a lookup table or database. In addition to the device identification, the controller 24 may further access an operating message or status of the surgical device 12, at step 94, based on the frequency identified from the identification signal 30. The message may correspond to a status or operating condition of the surgical device 12 or handpiece 14, which may be identified by the device controller 54 in response to an internal diagnostic test. Based on the device identification and/or the operating message or status of the connected device 34, the controller 24 may configure the operation of the control console 16 (step 96). Based on a control configuration identified from the identification signal 30, the controller 24 of the control console 16 may initiate the control and communication of the connected device 34 (step 98). Accordingly, the controller 24 may identify at least one of the device configuration 18 of the connected device 34 and the status based on the frequency of the identification signal 30, as previously discussed in reference to FIGS. 4A and 4B. Following step 98, the method 80 may be repeated periodically or in response to the connection of a surgical device and may continue throughout the operation of the control console 16 (step 100).

Referring generally, to FIGS. 1-6, various aspects of the system 10 are discussed in reference to operating configurations of one of more of the surgical devices 12 in further detail. As discussed in various examples provided herein, the control and communication to and from the surgical device 12 may be tailored based on the specific device configuration 18. For example, the control instructions communicated to and the interpretation of signals received from the connected device 34, collectively referred to as the control configuration of the controller 24, may be adjusted in response to various preconfigured or custom configurations accessed from the memory 42 of the controller 24. Additionally, the control configuration for the connected device 34 may be adjusted or corrected in response to the message M and corresponding status or operating instruction of the connected device 34. For example, in response to a message M indicating that the connected device 34 has an operating error the controller 24 may control the display/user interface 52 to present a message indicating that the control of the connected device is suspended due to the error. Additionally, one or more features (e.g., inputs, features, etc.) of the connected device 34 may be identified as being inoperable or having a fault status. In response to such messages M, the controller 24 may suspend or disable the functions or operating ranges identified by interpreting the message M. The suspended or disabled operations may be displayed on the display/user interface 52 in response to the control configuration accessed in the memory 42.

In some cases, the controller 24 may adjust the operation and/or appearance of the display/user interface 52 of the control console 16 to suit the functions and operating characteristics or data associated with the operation of the connected device 34 based on the different device configurations 18. For example, in response to the device configuration identifying a rotational actuator, the controller 24 may display a rotational direction and/or speed (e.g., rate of rotation in revolutions per minute [RPM]) of the connected device 34. Similarly, the controller 24 may display different operating information including, but not limited to, a current, frequency, relative intensity (e.g., low, medium, high, 1-10 range, a flow rate, vacuum pressure, etc.), or various operating information associated with the device configuration 18 and corresponding operation of the connected device 34. Accordingly, the disclosure provides for the controller 24 to identify the device configuration 18 associated with one or more connected devices 34 to assign corresponding control configurations tailored to the specific operating features and control signals of each of the connected devices 34. In this way, the system 10 may adjust a communication configuration of the communication port 20 and configure the controller 24 of the control console 16 in response to the frequency of the identification signal 30.

In some cases, the controller 24 may identify multiple surgical devices 12 in connection with the communication ports 20 and apply different control configurations for each of the surgical devices 12 based on the frequencies of the identification signals 30 communicated from each of the identification devices 32. For example, one or more of the first surgical device 12a, the second surgical device 12b, and the third surgical device 12c may be connected and interfaced with the controller 24 of the control console 16 via the communication ports 20 (see FIG. 1). As previously discussed, each of the device configurations 18 and the corresponding control configurations of the one or more connected devices 34 may be identified in response to an identifying frequency of identification signals 30. Based on the frequency, the device configuration 18 for each the connected devices 34 may be identified separately and distinctly assigned by the controller 24 to control the plurality of connected devices 34.

For example, the controller 24 may be configured to communicate via one or more communication protocols, input/output configurations and various control configurations, such that the inputs received from and the outputs directed to the connected device 34 are interpreted in accordance with preconfigured or custom control schemes for each of the device configurations 18 identified in the memory 42. Based on a control configuration identified in the memory 42 for a specific device ID indicated by the frequency of the identification signal, the controller 24 may apply an input/output control configuration associated with the connected device 34. Based on the control configuration, the controller 24 may configure the operation of the control console 16 to communicate control signals to and from the connected device 34 via a control configuration (e.g., identifiers, addresses, instructions, control ranges, drivers, etc.) to ensure that signals communicated from and received by the controller 24 are formatted in accordance with the input/output configuration for the device configuration 18 identified for the connected device 34.

Figure 6:
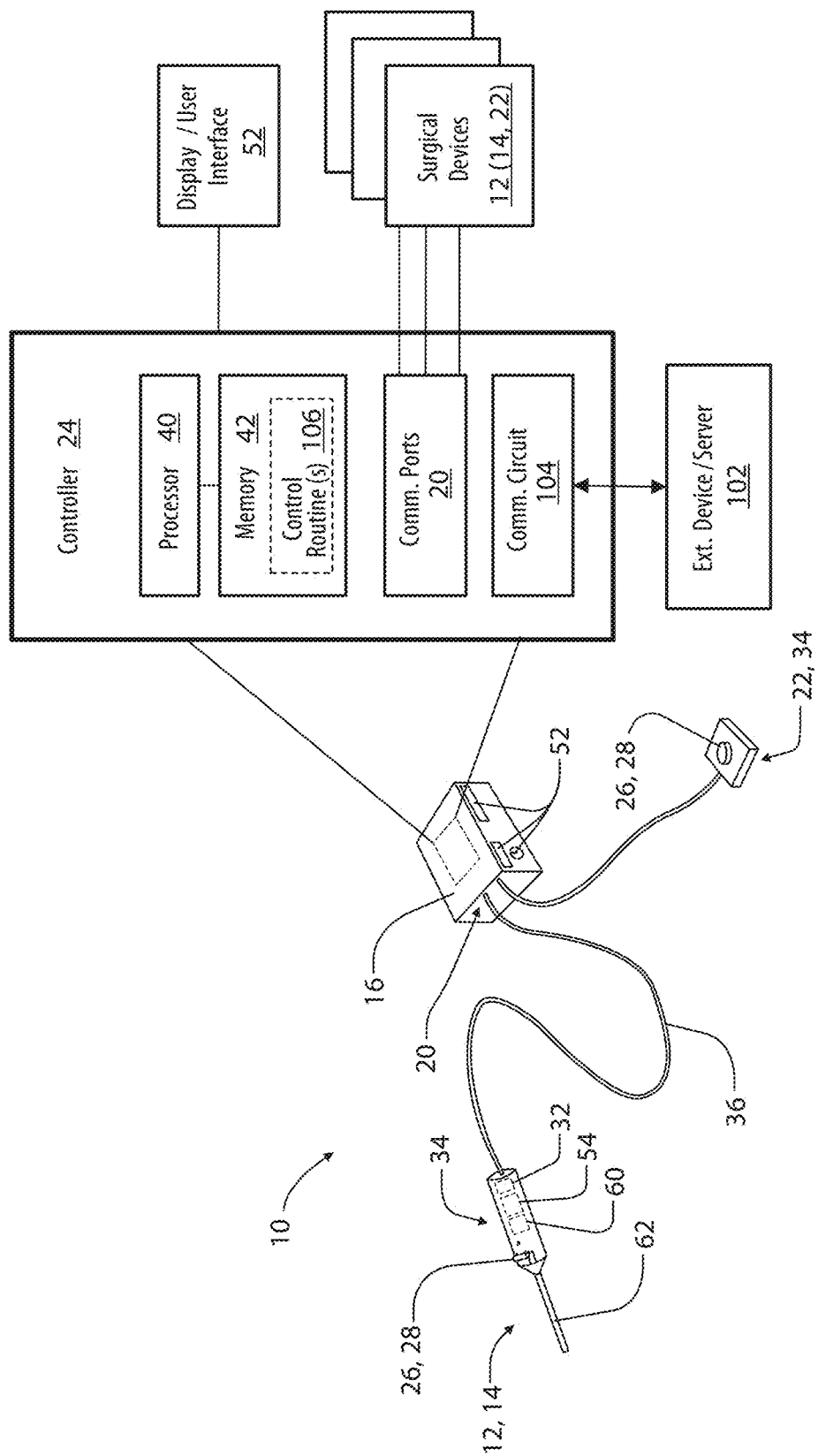
FIG. 6 is a block diagram demonstrating a surgical handpiece and control system for a control console in accordance with the disclosure.

Referring now to FIG. 6, the control system 10, as previously referenced in FIG. 1, is shown demonstrating the control console 16 and further details of the console controller 24. In operation, the controller 24 may receive inputs via one or more user interfaces 26 of the connected devices 34. In various examples, the operation of the system was discussed in reference to the operation of a single surgical device 12 or handpiece 14. However, it shall be understood that the operation of the system 10 may commonly provide for the concurrent use and control of two or more connected devices 34 in the form of surgical devices 12, which may include various handpieces 14, peripheral devices 22, remote controls, and various other devices or accessories that may be beneficial in a medical or surgical environment. For example, the surgical devices 12 may include various laser or radio frequency cutting or operating utilities in the form of ablation devices, catheters, pumps, suction or aspiration devices, and similar tools that may also correspond to handpieces 14. The surgical device 12 may correspond to one or more imaging device, which may be connected to the control console 16. The image data captured by such surgical devices 12 may be presented on the display/user interface 52 and/or may be displayed on one or more external devices 102 (e.g., peripherals, servers, communication networks, etc.) in communication with the control console 16 via the communication ports 20 or communication circuits 104. Accordingly, the control console 16 and corresponding operation of the identification module or device 32 of the surgical devices 12 may be applied by the controller 24 to configure the operation of the communication ports 20 to suit various device configurations 18.

As previously discussed, the peripheral devices 22 may correspond to surgical devices 12 or accessories associated with the operation of the control console 16. For example, the peripheral devices 22 may correspond to one or more electronic or electromechanical buttons, triggers, or pedals (e.g., pressure sensitive or single actuation foot pedals), and additional devices communicatively connected to the communication ports 20. The display/user interface 52 of the control console 16 may include one or more switches, buttons, dials, and/or displays, which may include soft-key or touchscreen devices incorporated in a display (e.g., liquid crystal display [LCD], light emitting diode [LED] display, cathode ray tube [CRT], etc.). In response to inputs received from the display/user interface 52, the controller 24 may activate or adjust the settings of the control signals communicated to the surgical devices 12. The control signals generated by the console controller 24 may be configured for operation in response to the device configuration 18 identified from the frequency of the identification signal 30. The output signals communicated from the communication ports 20 to the surgical devices 12 or handpieces 14 may be generated by various signal generators, motor controllers, or power supplies that may provide for operation of power electronic operations (e.g., motor drive signals and supply current), which may be controlled and configured for operation based on the instructions, commands, or signals communicated from the processor 40 of the console controller 24 for the associated device configuration 18. Accordingly, the console controller 24 may be operable to generate signals to drive or control the motion, rotation, activation, intensity, and various other operating characteristics of the connected devices 34.

The performance or specifications of the control console 16 (e.g., rating of power supply 50, heat dissipation, etc.) may be designed to accommodate the target properties of the control signals for each of the surgical devices 12 and peripheral devices 22 associated with the system 10. The processor 40 of the controller 24 or, more generally, the processors 40, 56 discussed herein may be implemented as microprocessors, microcontrollers, application-specific integrated circuits (ASIC), or other circuitry configured to perform instructions, computations, and control various input/output signals to control the control system 10. The instructions and/or control routines 106 of the system 10 may be accessed by the processors 40, 56 via a memory 42, 58. The memory 42, 58 may comprise random access memory (RAM), read only memory (ROM), flash memory, hard disk storage, solid state drive memory, etc. Each of the processors 40, 56 and memory devices 42, 58 may be implemented to suit the corresponding functionality or sophistication of the surgical devices 12 and the corresponding control requirements of the controller 24.

The controller 24 may incorporate additional communication circuits or input/output circuitry represented in FIG. 6 as a communication circuit 104, which may be implemented to communicate with one or more peripherals, devices, remote computers or servers, etc. The communication circuit 104 may complement or support the operating capability of the communication ports 20. In general, the communication circuit 104 may provide for communication via a variety of communication protocols to support operation of the surgical devices 12 and peripheral devices 22 in addition to the communication of the identification signal 30 as discussed herein. In an exemplary embodiment, the circuitry associated with the communication ports may include digital-to-analog converters, analog-to-digital converters, digital inputs and outputs, as well as one or more communication interfaces or buses. The communication interfaces of the communication ports 20 and/or the communication circuit 104 may be implemented with various communication protocols, such as serial communication (e.g., CAN bus, I2C, etc.), parallel communication, or network communication (e.g., RS232, RS485, Ethernet). In some cases, the communication circuit 104 may also provide for wireless network communication (Wi-Fi, Bluetooth®, Ultra-wideband [UWB], etc.). In some examples, the controller 24 may be in communication with one or more of the external devices 102 (e.g., control devices, peripherals, servers, etc.) via the communication circuitry 104. Accordingly, the control console 16 may provide for communication with various devices to update, maintain, and control the operation of the control system 10.

It will be understood that any described processes or steps within the described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structures and methods without departing from the concepts of the present device, and further it is to be understood that such concepts are intended to be covered by the following claims unless these claims by their language expressly state otherwise.

The above description is considered that of the illustrated embodiments only. Modifications of the device will occur to those skilled in the art and to those who make or use the device. Therefore, it is understood that the embodiments shown in the drawings and described above are merely for illustrative purposes and not intended to limit the scope of the device, which is defined by the following claims as interpreted according to the principles of patent law, including the Doctrine of Equivalents.

What is claimed:

1. A system comprising a control console configured to interchangeably control a plurality of surgical devices, wherein each of the plurality of surgical devices communicates an identification signal at a different fixed frequency defined by an identification device according to a device configuration, the system comprising:
   at least one communication port in connection with the control console that receives a communication cable configured to communicatively connect to the plurality of surgical devices; and a controller in communication with the at least one communication port, the controller configured to:
  in response to a connection of at least one of the plurality of surgical devices, supply an activation signal via the at least one communication port to at least one connected device of the plurality of surgical devices, wherein the device configuration of the at least one connected device is unidentified by the controller upon the connection;
  receive the identification signal from the identification device of the at least one connected device in response to the activation signal;
  identify a fixed frequency of the identification signal from the different fixed frequencies; and
  in response to the fixed frequency of the identification signal, identify the device configuration of the connected device.

2. The system according to claim 1, wherein the controller is further configured to:
  apply a control configuration of the control console in response to the device configuration and supply control signals to the connected device according to the control configuration, and wherein the control configuration comprises at least one of the following configurations of the connected device:
  an operating range of an actuator of the connected device;
  an input configuration; and
  a control signal protocol.

3. The system according to claim 1, wherein the controller is further configured to:
  apply a distinct control configuration for each of the plurality of surgical devices in response to each of the different fixed frequencies.

4. The system according to claim 3, wherein each of the plurality of different fixed frequencies is interpreted by the controller to distinguish the control configurations of the plurality of surgical devices.

5. The system according to claim 1, wherein the controller is further configured to:
  identify each of the surgical devices within one of a plurality of frequency ranges in response to the fixed frequency of the identification signal.

6. The system according to claim 5, wherein the frequency ranges are non-overlapping frequency bands and the controller distinctly identifies one of the plurality of surgical devices in response to the fixed frequency of the identification signal within each of the non-overlapping frequency bands.

7. The system according to claim 5, wherein the controller is further configured to:
  identify a plurality of messages for each of the surgical devices in response to a plurality of different periods of the fixed frequency of the identification signal within one of the frequency ranges, wherein each of the messages indicates a different control instruction or status indication of the connected device.

8. The system according to claim 1, wherein the control console further comprises a user interface, wherein the controller controls the user interface to display operating data in response to the device configuration of the connected device.

9. The system according to claim 1, wherein the controller is further configured to:
  identify a first device configuration of a first device of the plurality of surgical devices in response to a first frequency of a first identification signal; and
  identify a second device configuration of a second device of the plurality of surgical devices in response to a second frequency of a second identification signal.

10. The system according to claim 9, wherein the controller is further configured to:
  supply first control signals to the first device via a first channel of the plurality of channels based on a first control configuration identified in response to the first device configuration; and
  supply second control signals to the second device via a second channel of the plurality of channels based on a second control configuration identified in response to the second device configuration, wherein the first control configuration and the second control configuration are concurrently applied by the controller.

11. A method for controlling a plurality of surgical devices via a plurality of compatible control consoles, the method comprising:
  supplying an activation signal to a connected device via a communication port;
  receiving an identification signal from an identification device of the connected device;
  identifying a frequency of the identification signal originating from the identification device of the connected device, wherein the frequency is preconfigured to the identification device;
  in response to the frequency, identifying a device configuration of the connected device among a plurality of models, styles, or types of the plurality of surgical devices, wherein each of the device configurations is identified at a different fixed frequency based on the corresponding model, style, or type of the plurality of surgical devices by each of the compatible control consoles; and
  controlling an operation of the connected device in response to the device configuration.

12. The method according to claim 11, wherein each of the surgical devices is identified in response to the frequency of the identification signal within a frequency range associated with the device configuration and further comprising:
  identifying a status of the connected device in response to the frequency of the identification signal within a first range of frequency ranges, the first range corresponding to the first device.

13. A surgical device controlled by a control console and configured to control a plurality of compatible surgical devices, the device comprising:
  a device body;
  an identification circuit in connection with the device body; and
  a wired communication interface configured to communicatively connect the identification circuit to the control console, wherein:
  in response to receiving an energization signal from the control console via the wired communication interface, the identification circuit activates an identification signal at a fixed frequency and communicates the identification signal to the control console via the wired communication interface, wherein the identification signal is defined by the identification circuit and communicates a device type or a device configuration distinguishing the surgical device among the plurality of compatible surgical devices; and
  wherein each of the plurality of compatible surgical devices communicates the identification signal at a different fixed frequency defined by the identification circuit according to the device type or the device configuration of the connected device, and wherein the controller assigns a control configuration of the connected device based on the device type or the device configuration.

14. The surgical device according to claim 13, further comprising:
an accessory actuator configured to control a movement of a connected accessory; and
a device controller disposed in the device body and configured to control the operation of the accessory actuator in response to control signals received from the control console.

15. The surgical device according to claim 13, wherein the control configuration of the surgical device is initially unidentified by the device controller and identified by the controller responsive to the device type or the device configuration.

16. The surgical device according to claim 13, wherein the controller communicates control signals to the surgical device adjusting the operation of the surgical device based on the control configuration.

17. The system according to claim 1, wherein the device configuration is identified by accessing stored data identifying the connected device among a plurality of models, styles, or types of the plurality of surgical devices in response to the fixed frequency of the identification signal.

18. The system according to claim 1, wherein the controller is further configured to:
control the a least one connected device based on the device configuration following a termination of the identification signal at the fixed frequency.

19. The system according to claim 1, wherein the identification signal is communicated by the identification device for a predetermined period of time, and following the predetermined period of time, the identification signal is terminated, and the controller controls the device based on the identified device configuration.

* * * * *